US011039850B2

(12) United States Patent
Lee et al.

(10) Patent No.: US 11,039,850 B2
(45) Date of Patent: Jun. 22, 2021

(54) ENDOSCOPIC TOOL WITH SUCTION FOR FACILITATING INJECTION OF A FLUID INTO A SUBMUCOSAL LAYER OF TISSUE

(71) Applicant: GI SUPPLY, Mechanicsburg, PA (US)

(72) Inventors: Patrick Lee, Long Grove, IL (US); Heather Benoit, Round Rock, TX (US); Logan Castillo, Round Rock, TX (US); Joanna Rosenbaum, Chicago, IL (US)

(73) Assignee: GI SUPPLY, Mechanicsburg, PA (US)

( * ) Notice: Subject to any disclaimer, the term of this patent is extended or adjusted under 35 U.S.C. 154(b) by 298 days.

(21) Appl. No.: 16/128,247

(22) Filed: Sep. 11, 2018

(65) Prior Publication Data
US 2019/0262020 A1    Aug. 29, 2019

Related U.S. Application Data

(60) Provisional application No. 62/636,643, filed on Feb. 28, 2018.

(51) Int. Cl.
*A61B 17/30*    (2006.01)
*A61B 17/34*    (2006.01)
(Continued)

(52) U.S. Cl.
CPC .......... *A61B 17/30* (2013.01); *A61B 1/00094* (2013.01); *A61B 1/015* (2013.01);
(Continued)

(58) Field of Classification Search
CPC ..... A61B 17/30; A61B 17/3478; A61B 1/018; A61B 1/00094; A61B 1/015;
(Continued)

(56) References Cited

U.S. PATENT DOCUMENTS 4,723,940 A    2/1988   Wiegerinck
5,314,406 A    5/1994   Arias et al.
(Continued)

FOREIGN PATENT DOCUMENTS

WO    WO-0158361 A1    8/2001
WO    WO-2009006444 A1    1/2009
(Continued)

OTHER PUBLICATIONS

International Search Report received for PCT/US2018/050873 dated Dec. 11, 2018.
(Continued)

*Primary Examiner* — Bhisma Mehta
*Assistant Examiner* — Daniel Moore
(74) *Attorney, Agent, or Firm* — Marshall, Gerstein & Borun LLP

(57) ABSTRACT

An endoscopic tool for facilitating injection of fluid into a submucosal layer of tissue includes a first cannula, a suction source, a fluid lumen, and a second cannula. The first cannula has a suction surface disposed at a distal end, and defines a suction lumen. The suction source is coupled to the first cannula and creates a negative pressure within the suction lumen. The second cannula is disposed in a fluid lumen separate from the suction lumen, is adapted to be coupled to a source of fluid, and carries a needle at a distal end thereof. The tool draws the mucosal layer via the suction, which enlarges the submucosal layer, and injects a fluid into the enlarged portion of the submucosal layer via the needle, thereby creating a raised portion of tissue around the injection site.

31 Claims, 9 Drawing Sheets

(51) Int. Cl.
*A61B 1/018* (2006.01)
*A61B 1/00* (2006.01)
*A61M 5/315* (2006.01)
*A61B 1/015* (2006.01)
*A61B 17/00* (2006.01)

(52) U.S. Cl.
CPC .......... *A61B 1/018* (2013.01); *A61B 17/3478* (2013.01); *A61M 5/315* (2013.01); *A61B 2017/0034* (2013.01); *A61B 2017/00269* (2013.01); *A61B 2017/306* (2013.01)

(58) Field of Classification Search
CPC .... A61B 2017/00269; A61B 2017/306; A61B 2017/0034; A61B 17/00234; A61B 2017/00296; A61M 5/315; A61M 5/14
See application file for complete search history.

(56) References Cited

U.S. PATENT DOCUMENTS

| | | |
|---|---|---|
| 5,961,526 A | 10/1999 | Chu et al. |
| 6,358,197 B1 | 3/2002 | Silverman et al. |
| 6,454,702 B1 | 9/2002 | Smith |
| 6,524,234 B2 | 2/2003 | Ouchi |
| 6,537,205 B1 * | 3/2003 | Smith ................ A61B 1/015 600/104 |
| 6,558,314 B1 * | 5/2003 | Adelman ............. A61B 17/02 600/37 |
| 6,689,051 B2 | 2/2004 | Nakada et al. |
| 6,695,764 B2 | 2/2004 | Silverman et al. |
| 6,770,053 B2 | 8/2004 | Scarfone et al. |
| 6,796,963 B2 | 9/2004 | Carpenter et al. |
| 6,840,900 B2 | 1/2005 | Smith |
| 6,908,427 B2 | 6/2005 | Fleener et al. |
| 7,399,304 B2 | 7/2008 | Gambale et al. |
| 7,780,592 B2 | 8/2010 | Tronnes |
| 8,066,689 B2 | 11/2011 | Mitelberg et al. |
| 8,491,472 B2 | 7/2013 | Mitelberg et al. |
| 8,652,028 B2 | 2/2014 | Smith |
| 9,820,725 B2 | 11/2017 | Kogiso |
| 2001/0053909 A1 * | 12/2001 | Nakada ............... A61B 1/00089 606/47 |
| 2006/0095079 A1 | 5/2006 | Gerber |
| 2007/0129735 A1 | 6/2007 | Filipi et al. |
| 2009/0093670 A1 * | 4/2009 | Annest ................ A61M 29/02 600/16 |
| 2009/0198212 A1 | 8/2009 | Timberlake et al. |
| 2010/0160719 A1 * | 6/2010 | Kassab ............. A61M 25/0136 600/37 |
| 2013/0281780 A1 * | 10/2013 | Kadykowski ...... A61B 1/00119 600/116 |
| 2015/0018711 A1 * | 1/2015 | Furlong ............. A61B 1/00094 600/565 |
| 2015/0045825 A1 * | 2/2015 | Caplan ................ A61B 5/0036 606/191 |
| 2016/0361051 A1 | 12/2016 | Harris et al. |
| 2017/0007324 A1 | 1/2017 | Kadamus et al. |
| 2017/0354782 A1 * | 12/2017 | Quinn .................... A61M 5/24 |
| 2018/0036514 A1 | 2/2018 | Kassab et al. |
| 2018/0140169 A1 | 5/2018 | Mikkaichi |

FOREIGN PATENT DOCUMENTS

| | | |
|---|---|---|
| WO | WO-2013/159066 A1 | 10/2013 |
| WO | WO-2014/162093 A1 | 10/2014 |

OTHER PUBLICATIONS

Written Opinion received for PCT/US2018/050873 dated Dec. 11, 2018.

International Application No. PCT/US2020/035803, International Search Report and Written Opinion, dated Aug. 18, 2020.

* cited by examiner

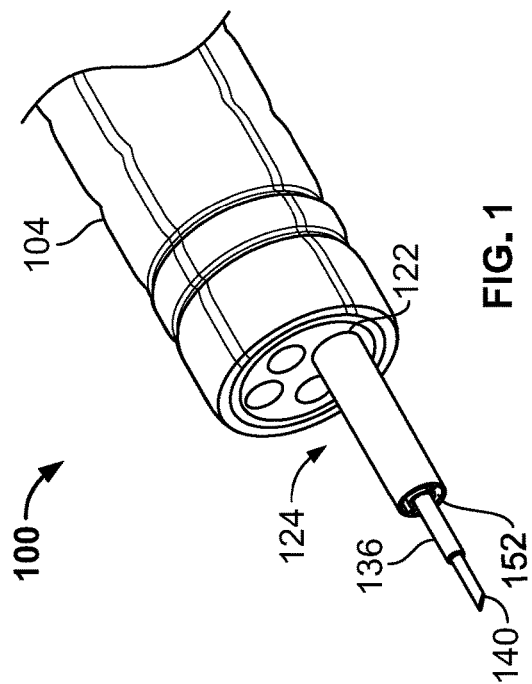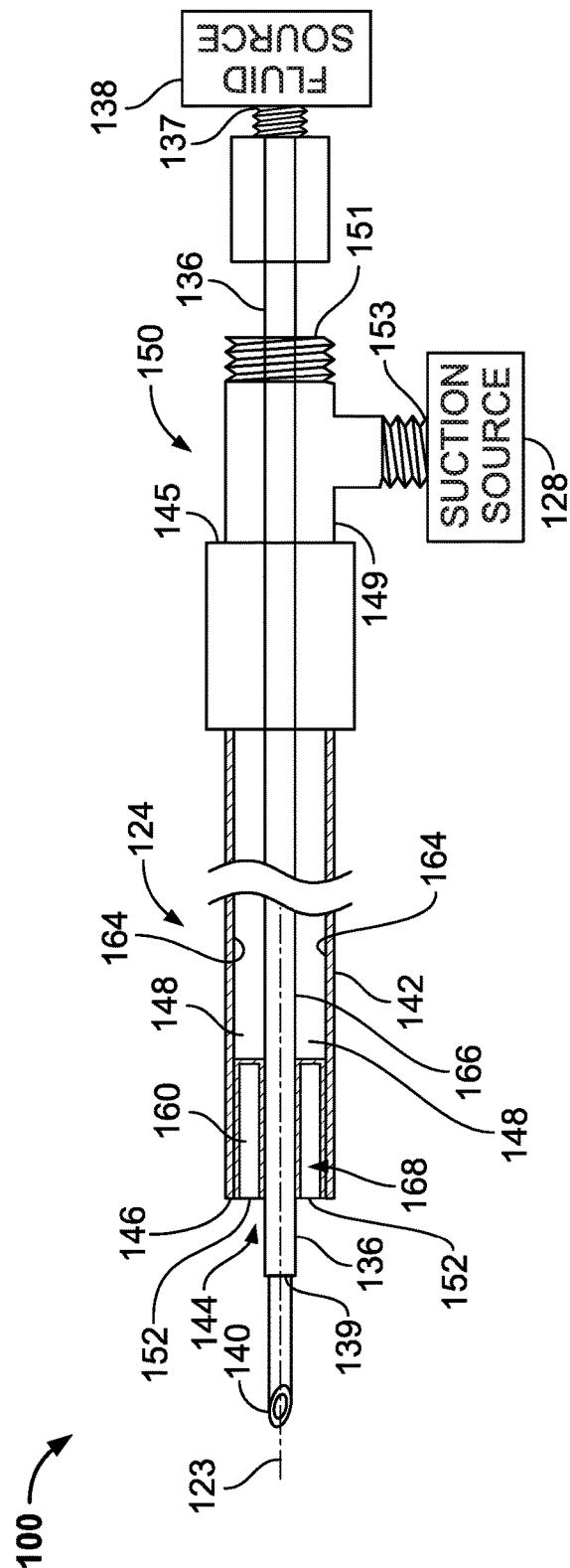

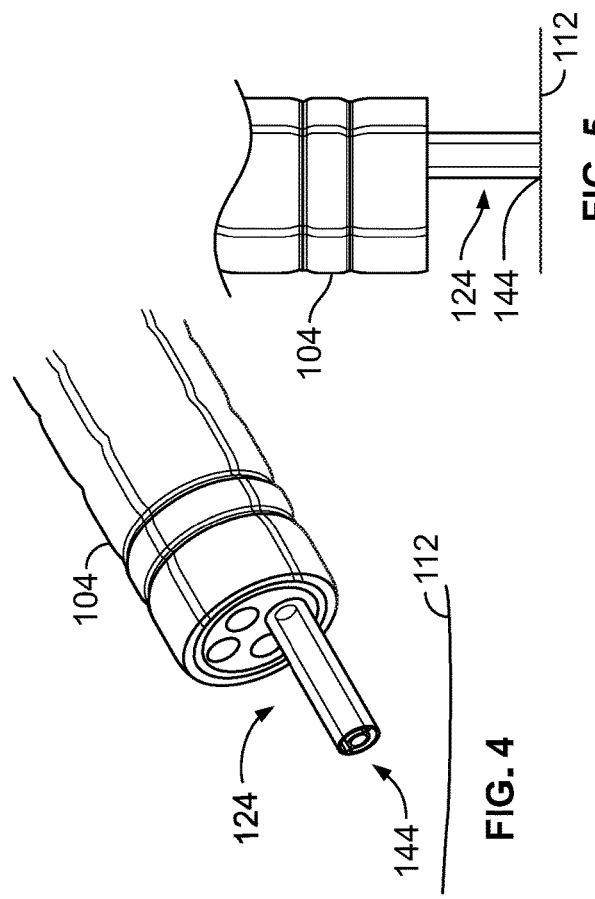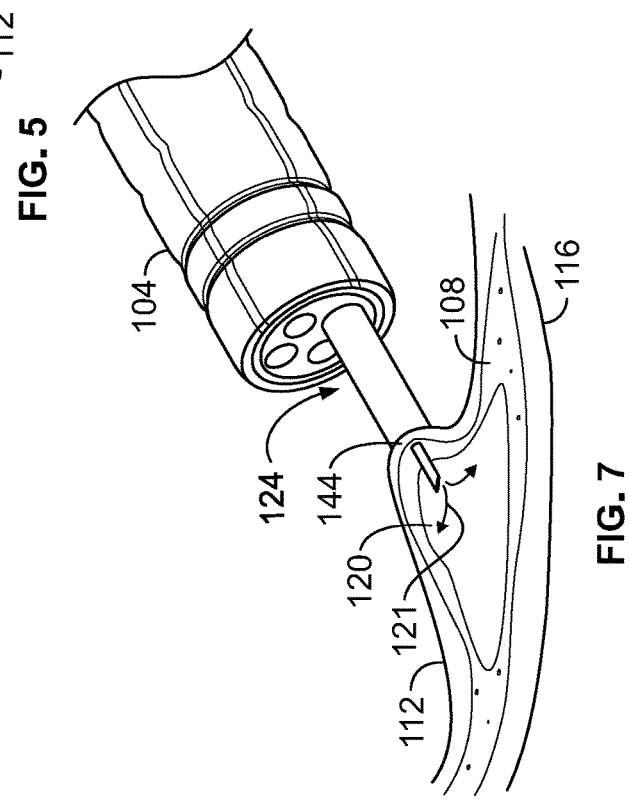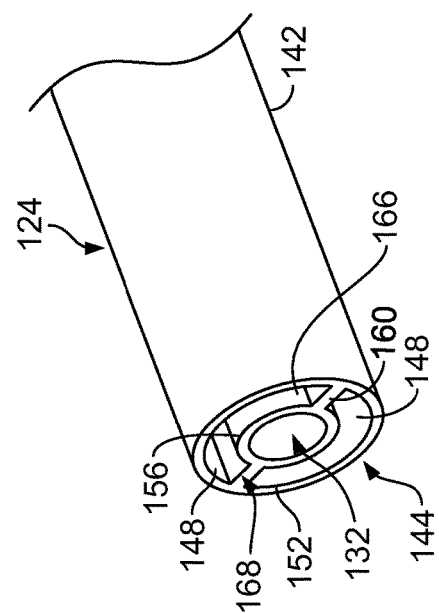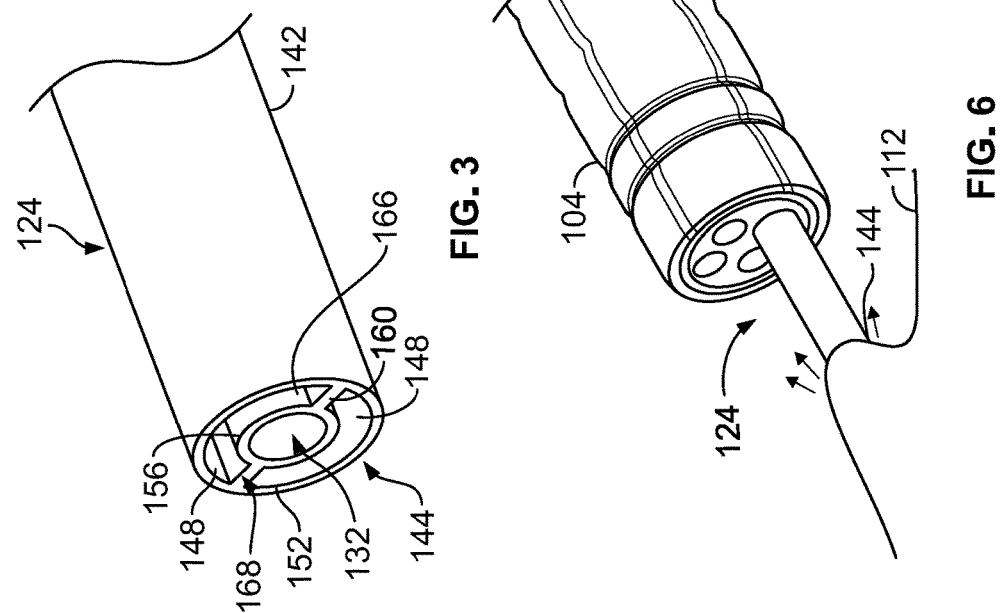

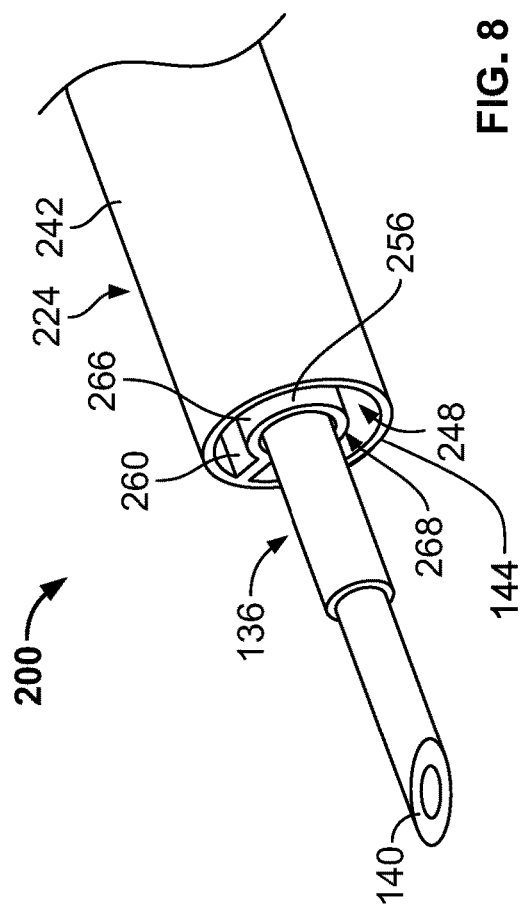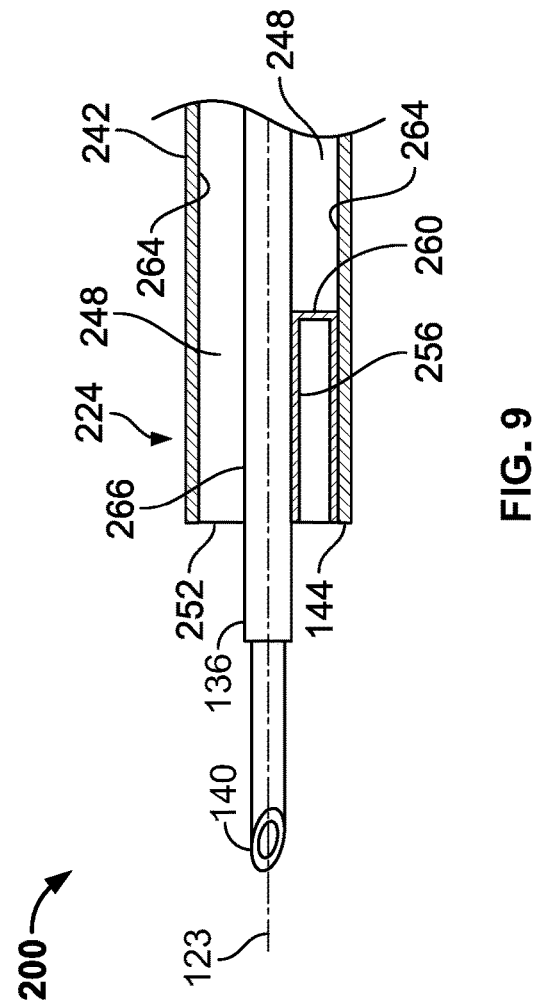

ENDOSCOPIC TOOL WITH SUCTION FOR FACILITATING INJECTION OF A FLUID INTO A SUBMUCOSAL LAYER OF TISSUE

CROSS-REFERENCE TO RELATED APPLICATIONS

This application claims priority benefit of U.S. Provisional Application No. 62/636,643, filed Feb. 28, 2018, the disclosure of which is incorporated by reference in its entirety.

FIELD OF THE DISCLOSURE

The present disclosure relates generally to endoscopic tools and, more particularly, to endoscopic tools with suction for facilitating injection of a fluid into a submucosal layer of tissue.

BACKGROUND

Doctors require endoscopes with various functionalities to perform various endoscopic procedures that a patient may undergo. As an example, doctors may need to inject fluid or another medical device into a submucosal layer of tissue, i.e., the layer of tissue between mucosa and muscle of a body part such as, for example, the colon. Ink may, for example, be used to mark (e.g., tattoo) a target area so as to let other doctors easily identify an area of interest located within the gastrointestinal tract. While numerous methods are known for injecting a fluid into the submucosal layer of tissue, these methods all require precise attention to detail and skill to ensure the needle is injected into the submucosal layer but not injected past the submucosal layer and into the muscle or other part of the gastrointestinal tract. If, for example, the needle is not injected into the submucosal layer or is injected past the submucosal layer, the doctor will inject the fluid into an incorrect location and either not mark the area properly or mistakenly mark another area of tissue, such as the peritoneal cavity. Further, improperly injecting the fluid into the submucosal layer may reduce the efficacy of the fluid injected. Additionally, these methods employ a needle that is always exposed, which may lead to inadvertent piercing of tissue in the gastrointestinal tract, potentially causing bleeding and lengthening of the procedure.

SUMMARY

In accordance with a first exemplary aspect of the present disclosure an endoscopic tool for facilitating the injection of a fluid into a submucosal layer of tissue is disclosed. The endoscopic tool includes a first cannula adapted to be slidably disposed within a lumen of an endoscope, a second cannula adapted to be coupled to a source of fluid to be delivered to the submucosal layer of tissue below a mucosal layer of tissue, and a needle stabilization structure coupled to the first cannula or the second cannula. The first cannula includes a suction surface and a suction lumen. The suction surface is disposed at a distal end of the first cannula to contact the mucosal layer of tissue. The suction lumen is formed within the first cannula between the suction surface and a proximal end of the first cannula. The second cannula is slidably disposed within a fluid lumen that is defined by the needle stabilization structure and is separate from the suction lumen. The second cannula carries a needle at a distal end of the second cannula. A suction source coupled to the first cannula creates a negative pressure within the suction lumen to draw the mucosal layer of tissue into contact with the suction surface. In response to the mucosal layer of tissue contacting the suction surface, the second cannula is movable toward the submucosal layer of tissue, causing the needle to pierce the mucosal layer of tissue and deliver the fluid into the submucosal layer of tissue.

In accordance with a second exemplary aspect of the present disclosure an endoscopic tool for facilitating the injection of a fluid to a submucosal layer of tissue is disclosed. The endoscopic tool includes a first cannula adapted to be disposed within a lumen of an endoscope, a second cannula disposed within a fluid lumen and adapted to be coupled to a source of fluid to be delivered to a submucosal layer of tissue, a needle stabilization structure coupled to the first cannula or the second cannula, and a needle carried by the second cannula. The first cannula includes a suction surface disposed at a distal end of the first cannula and configured to make contact with a mucosal layer of tissue. The needle stabilization structure defines at least one suction lumen and a fluid lumen that is separate from the suction lumen and is disposed centrally within the first cannula. The second cannula is movable between a first position, whereby the needle is disposed within the fluid lumen, and a second position, whereby the needle is disposed outside of the fluid lumen. A suction source coupled to the proximate end of the first cannula creates a negative pressure within the plurality of suction lumens to draw the mucosal layer of tissue against the suction surface. In response to the mucosal layer of tissue contacting the suction surface, the second cannula is movable from the first position to the second position, causing the needle to pierce the mucosal layer of tissue and deliver the fluid into the submucosal layer of tissue.

In accordance with a third exemplary aspect of the present disclosure, a method for injecting a fluid into a submucosal layer of tissue using an endoscopic tool is disclosed. The method includes disposing a first cannula within a lumen of an endoscope, the first cannula having a suction surface disposed at a distal end of the first cannula, and defining a suction lumen between the suction surface and a proximal end of the first cannula. The method includes disposing a second cannula carrying a needle within a fluid lumen separated from the suction lumen by a needle stabilization structure, and moving the first cannula from a first position, whereby the suction surface is disposed within the lumen of the endoscope, to a second position, whereby the suction surface is disposed outside of the lumen of the endoscope and proximate to a target area within a patient. The method includes creating a negative pressure in the suction lumen via a suction source coupled to the first cannula. The negative pressure draws the mucosal layer of tissue at the target area into contact with the suction surface. The method includes moving the first cannula away from the target area, thereby enlarging a submucosal layer of tissue below the mucosal layer of tissue at the target area. The method includes moving the second cannula from a first position, whereby the needle is disposed within the fluid lumen, to a second position, whereby the needle is disposed outside of the fluid lumen, such that the needle pierces the mucosal layer of tissue. Fluid is injected into the submucosal layer of tissue via the needle, thereby raising a portion of the mucosal layer of tissue in the target area.

BRIEF DESCRIPTION OF THE DRAWINGS

The features of this disclosure which are believed to be novel are set forth with particularity in the appended claims.

The present disclosure may be best understood by reference to the following description taken in conjunction with the accompanying drawings, in which like reference numerals identify like elements in the several figures, in which:

FIG. 1 is an example of a portion of an endoscopic tool constructed in accordance with the teachings of the present disclosure and disposed in a lumen of an endoscope.

FIG. 2 is a cross-sectional view of the endoscopic tool of FIG. 1.

FIG. 3 is a perspective view of the endoscopic tool of FIG. 2, but with the needle removed for clarity.

FIG. 4 illustrates the endoscopic tool of FIG. 1 positioned in the vicinity of a target area of tissue.

FIG. 5 illustrates the endoscopic tool of FIG. 1 positioned against the target area of tissue.

FIG. 6 illustrates the endoscopic tool of FIG. 1 interacting with the target area of tissue.

FIG. 7 illustrates the endoscopic tool of FIG. 1 injecting a fluid into a submucosal layer of tissue at the target area of tissue.

FIG. 8 is a perspective view of a portion of another example of an endoscopic tool constructed in accordance with the teachings of the present disclosure.

FIG. 9 is a side, cross-sectional view of the endoscopic tool of FIG. 8.

DETAILED DESCRIPTION

Figure 10:
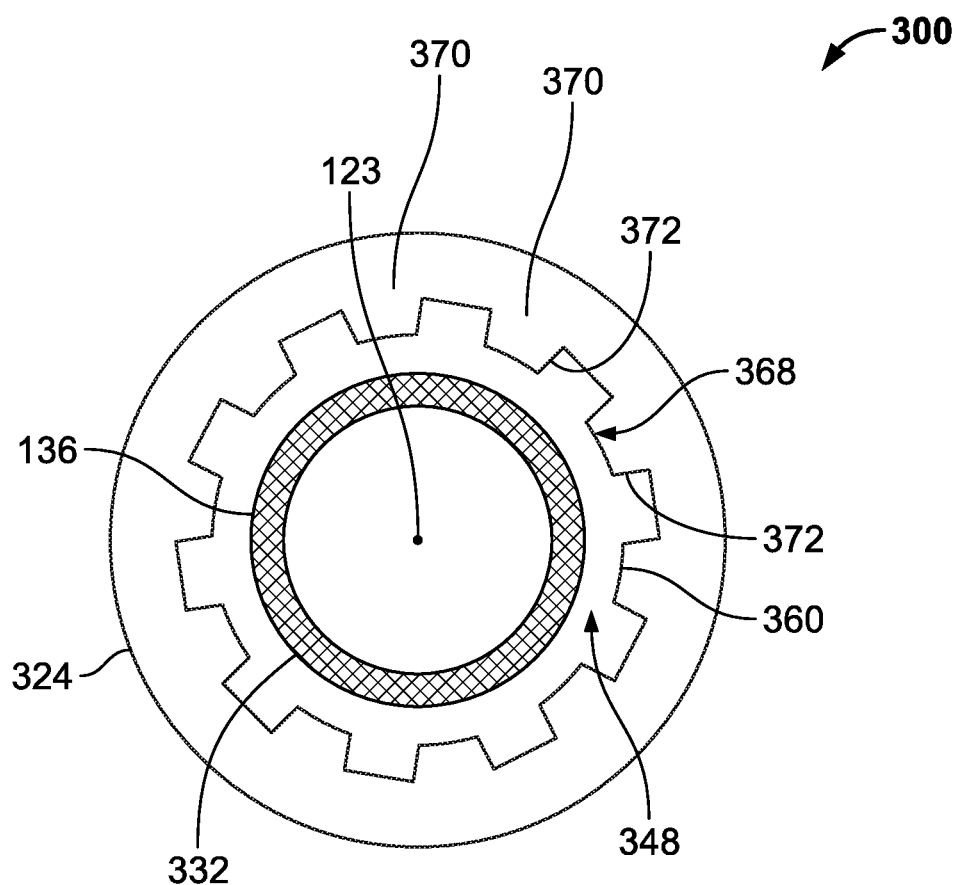
FIG. 10 is a cross-sectional view of another example of an endoscopic tool constructed in accordance with the teachings of the present disclosure.

The present disclosure is generally directed to an endoscopic tool for facilitating injection of a fluid into a submucosal layer of tissue. The endoscopic tool disclosed herein substantially mitigates the possibility that a needle carried by the tool will not be properly inserted into a target area of tissue (by, e.g., inserting the needle past the mucosal layer of tissue or the layer of muscle, causing a marking fluid to spill out rather than be injected into a submucosal layer of tissue). The endoscopic tool disclosed herein substantially mitigates that possibility by applying suction to tissue in the target area to draw and hold the tissue against the endoscopic tool, so that the tissue may be manipulated to create an enlarged portion of the tissue suitable for receiving the needle.

FIGS. 1-7 depict one example of an endoscopic tool 100 constructed in accordance with the principles of the present disclosure. The endoscopic tool 100 in this example is specifically designed for use with an endoscope 104 to mark a target area of tissue, in this case a portion of a submucosal layer 108 of tissue, in a patient during endoscopic procedures performed on the patient. More particularly, the endoscopic tool 100 in this example is specifically designed to be partially inserted into a working channel 122 of the endoscope 104. The endoscopic tool 100 effectively marks the desired portion of the submucosal layer 108 of tissue by using suction to draw and hold a mucosal layer 112 of tissue located above the portion of the submucosal layer 108 of tissue away from a layer of muscle 116 located below the portion of the submucosal layer 108 of tissue, thereby enlarging a portion 120 of the submucosal layer 108, and then injecting a fluid 121 into the enlarged portion 120. In this example, the fluid is a marking fluid (e.g., ink, a tattooing agent). In other examples, however, the endoscopic tool 100 may be utilized in other ways, e.g., to inject a different type of fluid (e.g., saline, epinephrine, a lifting agent), therapeutic, or other diagnostic agent into the submucosal layer 108 of tissue, in other types of procedures, etc.

The endoscopic tool 100 is preferably made from polyvinyl chloride ("PVC"), although it will be appreciated that the endoscopic tool 100 may instead be manufactured out of a different polymer, such as, latex rubber, polytetrafluoroethylene ("PTFE" or "Teflon") coated latex, polyether ether ketone ("PEEK"), polyether block amide, or polypropylene. The working channel 122, which in this example has a cylindrical shape, preferably has an inner diameter of 2.8 millimeters ("mm"), 3.7 mm, or 4 mm, though other endoscopes having differently sized working channels may be used.

The endoscopic tool 100 in this example generally includes a first cannula 124 having a fluid lumen 132, a suction source 128 coupled to the first cannula 124, a second cannula 136 that is disposed within the fluid lumen 132 and is adapted to be coupled to a source 138 of the marking fluid 121 (the source 138 may be carried by or separate from the second cannula 136), and a needle 140 carried by the second cannula 136 and configured to deliver the marking fluid 121 from the source 138 to the desired portion of the submucosal layer 108. In other examples, however, the endoscopic tool 100 may include different, additional, or fewer components.

In particular, the first cannula 124 includes a cannula body 142 and a stabilization structure 168 coupled to (e.g., integrally formed with, removably coupled to) the body 142 and configured to stabilize, and in some cases center, the second cannula 136 and the needle 140 during use of the tool 100. The cannula body 142 is sized to be at least partially disposed in the working channel 122 of the endoscope 104. Thus, at least in this example, the cannula body 142 has a cylindrical shape. The first cannula 124 has a suction surface 144 that is disposed at a distal end 146 of the cannula body 142 and, at least in this example, is oriented in a direction that is perpendicular to a length of the cannula body 142. Orienting the suction surface 144 in this manner allows for the mucosal layer 112 of tissue to be drawn evenly against a flat surface, such that when the mucosal layer 112 is drawn against the suction surface 144, the mucosal layer 112 sits flush with the suction surface 144 and is not drawn inside of the first cannula 124. In other examples, however, the suction surface 144 may be disposed proximate to but spaced from the distal end 146 of the cannula body 142. As an example, the suction surface 144 may be disposed at a secondary tip or tube that is secured to the distal end 146 of the cannula body 142. Moreover, in other examples, the suction surface 144 may be oriented in a direction that is angled, but not perpendicular, to the length of the cannula body 142.

Having the mucosal layer 112 of tissue sit directly flush against the suction surface 144 advantageously gives a user greater control over how far the needle 140 is inserted into the submucosal layer 108 of tissue and allows the user to have an unobstructed view of the target area of tissue. Moreover, this configuration does not utilize structural features that extend past the suction surface 144 (e.g., hoods, elongated projections, etc.) that disadvantageously interfere with the interface between the mucosal layer 112 of tissue and the suction surface 144. For example, drawing the mucosal layer 112 into a hood that extends outward of the suction surface 144 can cause the mucosal layer 112 to form a point or tip at the suction surface 144 rather than fully rest against the suction surface 114. This type of formation within the hood is undesirable because it may lead to the needle 140 not being fully inserted into the submucosal layer 108, thereby causing the marking fluid 121 to spill out of the tissue. These types of structural features also obstruct the user's view of imaging instruments used in conjunction with the endoscopic tool disclosed herein, causing a degree of uncertainty as to the location of the needle.

The first cannula 124 also includes at least one suction lumen 148 and the fluid lumen 132 mentioned above, each of which is at least partially defined by the stabilization structure 168. In this example, the stabilization structure 168 takes the form of an annular wall 156 and a pair of ribs 160 spaced apart from one another (e.g., 180 degrees apart from one another). The annular wall 156 is centrally disposed in the cannula body 142 and the ribs 160 each extend between an inner surface 164 of the cannula body 142 and an outer surface 166 of the annular wall 156. The annular wall 156 and the ribs 160 extend in this manner along the length of the cannula body 142, as illustrated. Thus, in this example, the first cannula 124 includes two suction lumens 148, with each suction lumen 148 having a semi-circular shape in cross-section and defined between a portion of the inner surface 164 of the cannula body 142, a portion of the outer surface 166 of the annular wall 156, and the ribs 160. In other examples, the first cannula 124 can include more or less and/or differently arranged suction lumens 148 in order to account for manufacturing needs. Additionally, in this example, the first cannula 124 includes a plurality of apertures 152 that are formed into the suction surface 144 and open into the suction lumens 148, which extend along a substantial portion of the entire length of the cannula body 142, as is depicted in FIG. 3.

Further in this example, the fluid lumen 132 is defined by the centrally located annular wall 156, such that the fluid lumen 132 is disposed along a central axis 123 of the first cannula 124. The fluid lumen 132 extends from the distal end 146 to a proximal end 145 of the cannula body 142. Thus, the fluid lumen 132 is surrounded by the suction lumens 148 and the centrally located annular wall 156 between the proximal end 145 and the distal end 146 of the first cannula 124. Additionally, the fluid lumen 132 and the suction lumens 148 are positioned and sized such that the marking fluid 121 flowing through the fluid lumen 132 and injected into the submucosal layer 108 does not flow into the suction lumens 148.

So configured, the first cannula 124 is configured to receive the second cannula 136 through an opening located at a proximal end 145 of the fluid lumen 132, such that the second cannula 136 is movable (e.g., slidable) through the fluid lumen 132. The second cannula 136 has a proximal end 137 and a distal end 139 opposite the proximal end 137. As illustrated, the proximal end 137 of the second cannula 136 is adapted to be coupled to the source 138 of the marking fluid 121 to be injected into the submucosal layer of tissue 108. The second cannula 136 also includes a needle 140 carried by and extending outward from the distal end 139. The needle 140 is configured to pierce the mucosal layer 112 of tissue and deliver the marking fluid 121 once the needle 140 is in the submucosal layer 108 of tissue. In this example, the needle 140 is fixedly secured to the distal end 139 of the second cannula 136 via a friction fit. Alternatively, in other examples, the needle 140 may be fixedly or removably secured to the distal end 139 of the second cannula 136 via, for example, a crimp or a clamp. Further, the second cannula 136 preferably has a length between two hundred (200) and two hundred and forty (240) centimeters ("cm") long. Further yet, the needle 140 is preferably a 23 or 25 gauge needle that is between one (1) and five (5) mm and more preferably, between one (1) and two and a half (2.5) mm long.

In this example, the suction source 128 is coupled to the first cannula 124 at the proximal end 145 of the first cannula 124. More particularly, in this example, the suction source 128 is coupled to the first cannula 124 via a connector in the form of a "T" connector 150 with three ports disposed at and coupled to the proximal end 145 of the first cannula 124. A first port 149 of the "T" shaped connector 150 is inserted into a port at the proximal end 145 of the first cannula 124. A second port 151 of the connector 150 is co-axial with the first port 149 and slidably receives the second cannula 136. While not illustrated herein, in at least this example, a sealing element (e.g., an O-ring, sealing grease) is disposed in the second port 151 to fluidly isolate the suction lumen 148 from the working lumen 132 and from the atmosphere, ensuring that a vacuum is created in the first cannula 124. A third port 153 of the connector 150 is perpendicular to the first and second ports 149, 151 and is configured to receive the suction source 128, such that the suction lumens 148 are in fluid communication with the suction source 128. In this example, the suction source 128 is threaded onto the third port 153. It will be appreciated, however, that the suction source 128 may be attached to the third port 153 in other ways (e.g., friction fit, twist lock, etc.). It will be appreciated that the suction source 128 may be a vacuum pump, a hospital wall suction outlet, a hand crank, or an endoscope tower.

In any case, by coupling the first cannula 124 to the suction source 128 in this manner, the suction source 128 may create a negative pressure in the plurality of suction lumens 148. This negative pressure, or suction, draws and holds the mucosal layer 112 to and against the suction surface 144. By holding the mucosal layer 112 against the suction surface 144, the endoscopic tool 100 allows the user to manipulate the mucosal layer 112 to, for example, enlarge a portion of the submucosal layer 108 without losing contact with the mucosal layer 112, thereby facilitating a quick and accurate injection of the marking fluid 121 into the submucosal layer 108.

FIGS. 4-6 will now be referenced to discuss, in greater detail, the operation of the endoscopic tool 100. In operation, the endoscopic tool 100 is inserted into the working channel 122 of the endoscope 104 and the endoscope 104 is progressed through the gastrointestinal tract ("GI tract") until the target area of the GI tract is reached. The target area may, for example, be the location of a tumor or the location of a polyp. As depicted in FIG. 4, the endoscopic tool 100 is moved toward the mucosal layer 112 of tissue in that target area until the suction surface 144 is located proximate to the target area of tissue. Once the tool 100 is at the target area, the negative pressure created by the suction source 128 and in the suction lumens 148 draws the mucosal layer 112 to and against the suction surface 144, as depicted in FIG. 5. The negative pressure created in the suction lumens 148 is strong enough to draw the mucosal layer 112 and hold the mucosal layer 112 against the suction surface 144, but is not strong enough to damage the mucosal layer 112 or pull the mucosal layer 112 into or within the suction lumens 148 (i.e., within the interior of the cannula body 142).

As the negative pressure in the suction lumens 148 holds the mucosal layer 112 of tissue against the suction surface 144, the first cannula 124 can be moved toward the endoscope 104 and away from the submucosal layer 108, which pulls the mucosal layer 112 and the submucosal layer 108 away from the muscle layer 116, enlarging the portion 120 of the submucosal layer 108, as depicted in, for example, FIG. 6. This mitigates the potential for inserting the needle 140 past the submucosal layer 108 and into the muscle layer 116. Additionally, by keeping the mucosal layer 112 of tissue held against the suction surface 144, the tool 100 facilitates better control as to when the needle 140 pierces the mucosal layer 112, as the needle 140 will pierce the mucosal layer 112 only once the needle 140 is extended past the suction surface 144 of the first cannula 124.

Once the portion 120 has been sufficiently enlarged, the second cannula 136 disposed within the fluid lumen 132 is moved from a first position, in which the needle 140 is disposed within the fluid lumen 132, to a second position, in which the needle 140 is disposed outside of the fluid lumen 132, to pierce the mucosal layer 112. In this way, the needle 140 is not exposed until the target area in the GI tract is reached by the endoscopic tool 100. In doing so, inadvertent piercing of tissue by the needle 140 outside the target area is eliminated. In some examples, the second cannula 136 is manually movable to the second position by pushing the proximal end 137 of the second cannula 136 toward the endoscope 104. In other examples, the second cannula 136 is automatically movable to the second position (and back to the first position). The needle 140 may be manually or automatically advanced two (2) mm or less to pierce the mucosal layer 112 of tissue. In another example, the needle 140 may be manually or automatically advanced between four (4) to five (5) mm to pierce the mucosal layer 112 of tissue. While not illustrated herein, the tool 100 may include a needle stop that helps to guide the needle 140 to the proper position (for piercing the mucosal layer 112) and to prevent the needle 140 from being advanced beyond this position.

In any case, after the second cannula 136 is moved to the second position, the needle 140 will be disposed within the enlarged portion 120 as shown in FIG. 6. Once the needle 140 is placed in the desired location, the marking fluid 121 is passed through the second cannula 136, out of the needle 140, and into the submucosal layer 108. Injecting the marking fluid 121 into the enlarged portion 120 of the submucosal layer 108 raises the surrounding tissue and acts as a visual indicator to a user of the tool 100 that the injection has been properly performed. After the desired amount of marking fluid 121 is injected, the second cannula 136 may be retracted into the fluid lumen 132 and the first cannula 124 may also be retracted into the working channel 122 of the endoscope 104.

FIGS. 8 and 9 depict another example of an endoscopic tool 200 for facilitating fluid injection into the submucosal layer 108 of tissue. The endoscopic tool 200 depicted in FIGS. 8 and 9 is similar to the endoscopic tool 100 depicted in FIGS. 1 and 2, with common components depicted using common reference numerals, but is different in that the endoscopic tool 200 includes a first cannula 224 that, while otherwise similar, has a stabilization structure 268 that is different from the stabilization structure 168. Like the stabilization structure 168, the stabilization structure 268 locates and secures the second cannula 136 slidably disposed within the fluid lumen 132 so that it is disposed along the central axis 123 of the first cannula 224. However, unlike the stabilization structure 168, the stabilization structure 268 is formed from a single rib 260 and an annular wall 256. Thus, the stabilization structure 268 creates a single suction lumen 248 within the first cannula 224.

As with the stabilization structure 168, the stabilization structure 268 may extend the entire length of the first cannula 224 or, as depicted in FIG. 9, the stabilization structure 268 may only extend a portion of the length of the first cannula 224. In both cases, however, the stabilization structure 168, 268 is positioned immediately adjacent to the suction surface 144, such that the second cannula 136 will be less likely to move during use. While not illustrated herein, it will be appreciated that the stabilization structure 268 may be recessed within the first cannula 224 (i.e., spaced from the suction surface 144).

In this example, the annular wall 256 is centrally disposed in a cannula body 242 of the first cannula 224 and the rib 260 extends between an inner surface 264 of the cannula body 242 and an outer surface 266 of the annular wall 256. Thus, in this example, the first cannula 224 includes the single suction lumen 248, with the suction lumen 248 having a substantially circular shape in cross-section and defined between a substantial portion of the inner surface 264 of the cannula body 242, a substantial portion of the outer surface 266 of the annular wall 256, and opposing surfaces of the rib 260. Additionally, in this example, the first cannula 224 includes an aperture 252 that is formed into the suction surface 144 and opens into the suction lumen 248.

FIG. 10 depicts a portion of another example of an endoscopic tool 300 for facilitating fluid injection into the submucosal layer 108 of tissue. The endoscopic tool 300 of FIG. 10 is similar to the endoscopic tool 100 depicted in FIGS. 1 and 2, with common components depicted using common reference numerals, but is different in that the endoscopic tool 300 includes a first cannula 324 that has a stabilization structure 368 that is different from the stabilization structure 168. Like the stabilization structure 168, the stabilization structure 368 locates and secures the second cannula 136 slidably disposed within the first cannula 324 so that the second cannula 136 is disposed along the central axis 123 of the first cannula 324. However, unlike the stabilization structure 168, the stabilization structure 368 is integrally formed with an inner wall of the first cannula 324. In this example, the stabilization structure 368 takes the form of multiple ribs 370 that extend radially inward from the inner wall of the first cannula 324. The multiple ribs 370 form recessed spaces 372 between each of the ribs 370, which in turn define a suction lumen 348. The stabilization structure 368 also defines a fluid lumen 332 that is radially inward of and spatially separated from the suction lumen 348. Thus, when the second cannula 136 is slidably disposed within the fluid lumen 332, the suction source may create a negative pressure in the suction lumen 348.

Figure 11:
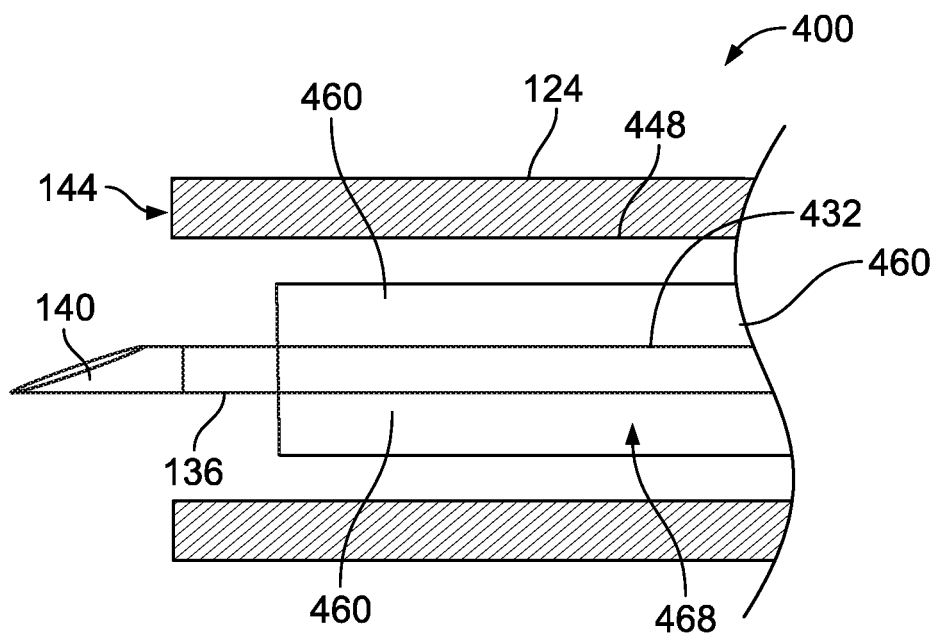
FIG. 11 is a cross-sectional view of a portion of another example of an endoscopic tool constructed in accordance with the teachings of the present disclosure.

FIG. 11 depicts yet another example of an endoscopic tool 400 for facilitating fluid injection into the submucosal layer 108 of tissue. The endoscopic tool 400 of FIG. 11 is similar to the endoscopic tool 100 depicted in FIGS. 1 and 2, with common components depicted using common reference numerals, but is different in that the endoscopic tool 400 includes a stabilization structure 468 that is different from the stabilization structure 168. Like the stabilization structure 168, the stabilization structure 468 locates and secures the second cannula 136 slidably disposed within the first cannula 168 so that the second cannula 136 is disposed along the central axis 123 of the first cannula 124. However, unlike the stabilization structure 168, the stabilization structure 468 is coupled to the second cannula 136 instead of the first cannula 124. In particular, the stabilization structure 468 includes a plurality of circumferentially arranged ribs 460 and a fluid lumen 432 that is defined by the ribs 460 and is sized to receive the second cannula 136. The ribs 460 extend radially outward, toward the first cannula 124, as shown in FIG. 11. In this example, the ribs 460 create a "+" shape when viewing a cross-section of the stabilization structure 468 (not shown), though in other examples, the ribs 460 can define a different cross-sectional shape. Additionally, the stabilization structure 468 may be integrally formed with or separately manufactured and coupled to the second cannula 136. In any case, it will be appreciated that the stabilization structure 468 structurally separates the fluid lumen 432 from a suction lumen 448 of the tool 400.

Figure 12:
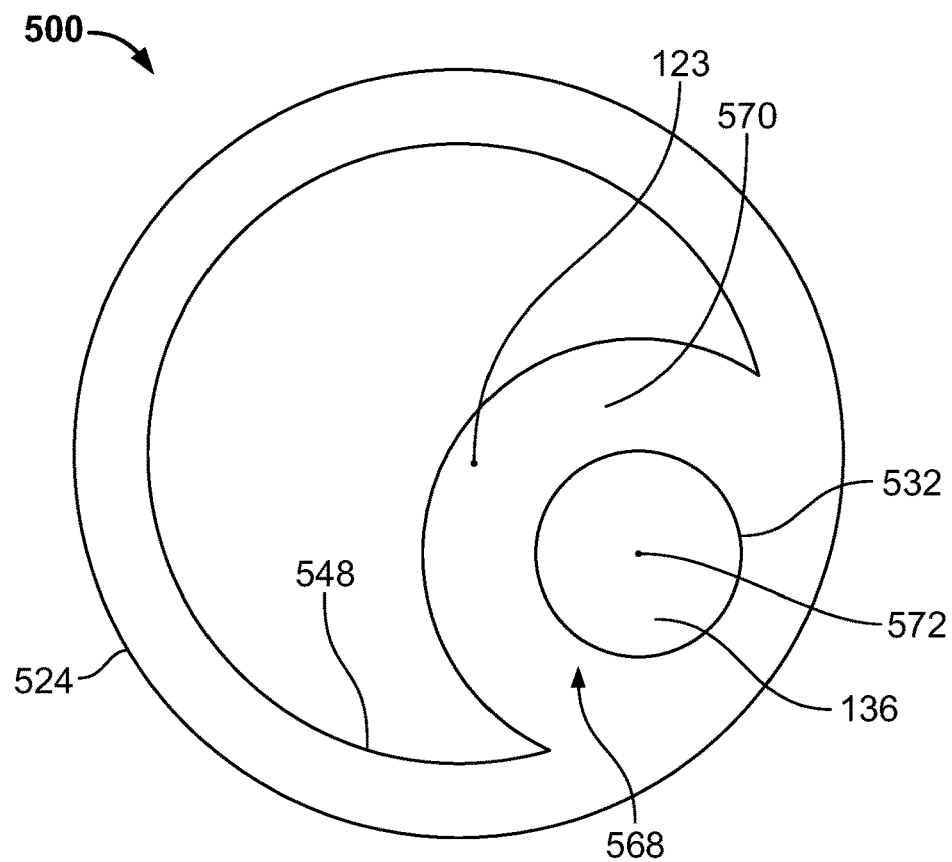
FIG. 12 is a cross-sectional view of a portion of another example of an endoscopic tool constructed in accordance with the teachings of the present disclosure.

FIG. 12 depicts a portion of yet another example of an endoscopic tool 500 for facilitating fluid injection into the submucosal layer 108 of tissue. The endoscopic tool 500 of FIG. 12 is similar to the endoscopic tool 100 depicted in FIGS. 1 and 2, with common components depicted using common reference numerals, but is different in that the endoscopic tool 500 includes a first cannula 524 that is different from the first cannula 124 described above. First, the first cannula 524 has a stabilization structure 568 that is different from the stabilization structure 168. Like the stabilization structure 168, the stabilization structure 568 locates and secures the second cannula 136 slidably disposed within the first cannula 524. However, unlike the stabilization structure 168, the stabilization structure 568 takes the form of a curved, substantially semi-circular wall 570 that extends between and connects different portions of the first cannula 524. Thus, while the stabilization structure 568 defines a fluid lumen 532 and a suction lumen 548 that is structurally separated from the fluid lumen 532, the wall 570 is positioned so that the suction lumen 548 has a crescent shape in cross-section and the fluid lumen 532 has a circular shape in cross-section, with the fluid lumen 532 offset from the central axis 123 of the first cannula 524. In turn, while the stabilization structure 568 locates and secures the second cannula 136 within the first cannula 524, the second cannula 136 is disposed along an axis 572 that is offset from the central axis 123 (rather than being disposed along the central axis 123).

Figure 13:
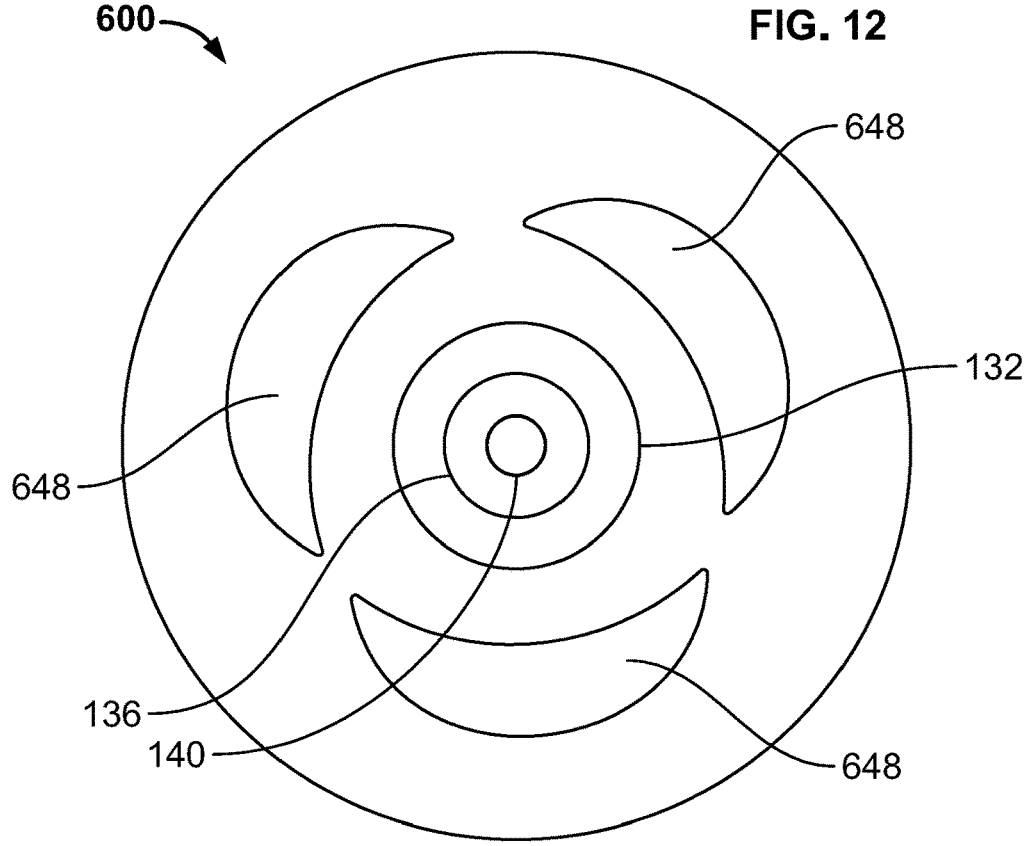
FIG. 13 is a cross-sectional view of a portion of another example of an endoscopic tool constructed in accordance with the teachings of the present disclosure.

FIG. 13 depicts yet another example of an endoscopic tool 600 for facilitating fluid injection into the submucosal layer 108 of tissue. The endoscopic tool 600 of FIG. 13 is similar to the endoscopic tool 100 depicted in FIGS. 1 and 2, with common components depicted using common reference numerals, but is different in that the endoscopic tool 600 includes three suction lumens 648 that are circumferentially arranged around the fluid lumen 132. Each of the three suction lumens 648 preferably has an arcuate shape in cross-section, as illustrated.

Figure 14:
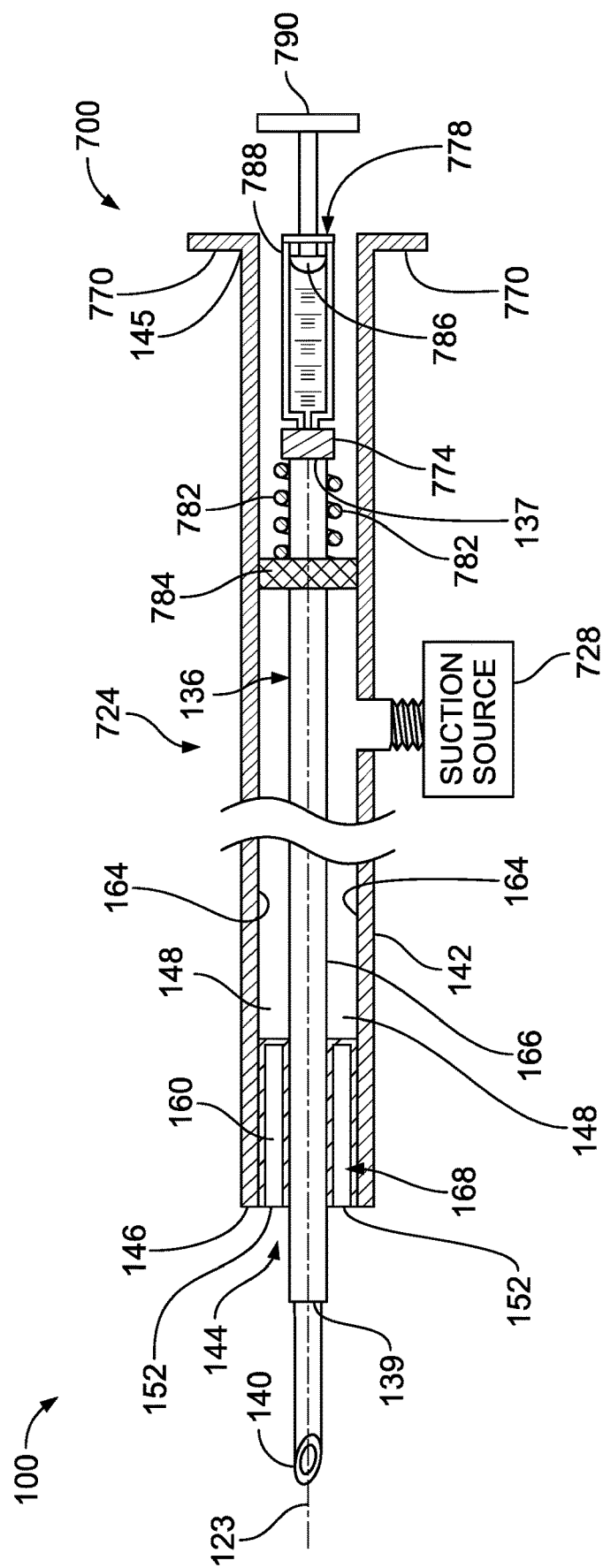
FIG. 14 is a cross-sectional view of another example of an endoscopic tool constructed in accordance with the teachings of the present disclosure.

FIG. 14 depicts another example of an endoscopic tool 700 for facilitating fluid injection into the submucosal layer 108 of tissue. The endoscopic tool 700 depicted in FIG. 14 is similar to the endoscopic tool 100 depicted in FIGS. 1 and 2, with common components depicted using common reference numerals, but is different in that the endoscopic tool 700 has a first cannula 724 that is different from the first cannula 124, and a fluid injection system 778 that facilitates a quick and easy delivery of the marking fluid 121 into the submucosal layer 108. In particular, the fluid injection system 778 acts to translate the second cannula 136 forward, to its second position, while the marking fluid 121 is simultaneously injected into the submucosal layer 108.

The first cannula 724 in this example is substantially similar to the first cannula 124 described above, but also includes an annular flange 770 that protrudes outward from the cannula body 142 at or proximate to the proximal end 145. While not illustrated herein, the annular flange 770 is arranged to engage a portion of the endoscope 100 to properly seat the tool 700 within the endoscope 100, and serves as a gripping surface that helps a user of the tool 700 deliver marking fluid 121 into the submucosal layer 108 via the fluid injection system 778.

Meanwhile, the fluid injection system 778 is coupled to the proximal end 137 of the second cannula 136 to supply the marking fluid 121 as desired. In this example, the fluid injection system 778 includes a stopper 784, a spring 782, a fluid source 788 containing the marking fluid 121 is fluidly coupled to the second cannula 136 via an adapter 774, a plunger 786, and an actuating element 790. The stopper 784, which is movably disposed within the first cannula 724 and is carried by the second cannula 136 between a suction source 728 (identical to the suction source 128) and the proximal end 145 of the first cannula 724, seals the interior of the first cannula 724, thereby fluidly isolating the suction lumen 148 from the atmosphere. The spring 782 is seated against and disposed between the stopper 784 and the adapter 774, such that the spring 782 is operatively coupled to the stopper 784. The fluid source 788 is fluidly coupled to the proximal end 137 of the second cannula 136 via the adapter 774. In this example, the fluid source 788 is a syringe that contains the marking fluid 121, though in other examples, the fluid source 788 can take a different form. The plunger 786 is movably disposed within the syringe 788 to help eject the marking fluid 121 from the syringe 788 when desired. Finally, the actuating element 790 in this example takes the form of a handle that is integrally formed with the plunger 786 but extends outside of the syringe 788 to allow the user to actuate the fluid injection system 778 to deliver the marking fluid 121.

In operation, to inject the needle 140 into the submucosal layer 108 and inject the marking fluid 121, the user may activate the fluid injection system 778 by, for example, placing a finger on the flange 770 and a thumb on the actuation element 790, and moving the actuation element 790, and, in turn, the plunger 786 forward (i.e., toward the suction surface 144). Moving the actuation element 790 forward moves the plunger 786 forward within the syringe 788, thereby forcing the marking fluid 121 in the syringe 788 through and out of the syringe 788 and into and through the second cannula 136. Moving the actuation element 790 forward in this manner also simultaneously causes the spring 782 to compress and drive the stopper 784 forward, toward the suction surface 144, which, in turn, drives the second cannula 136 to its second position, such that the needle 140 is disposed within the enlarged portion 120 and the marking fluid 121 is delivered into the submucosal layer 108 of tissue.

Figure 15:
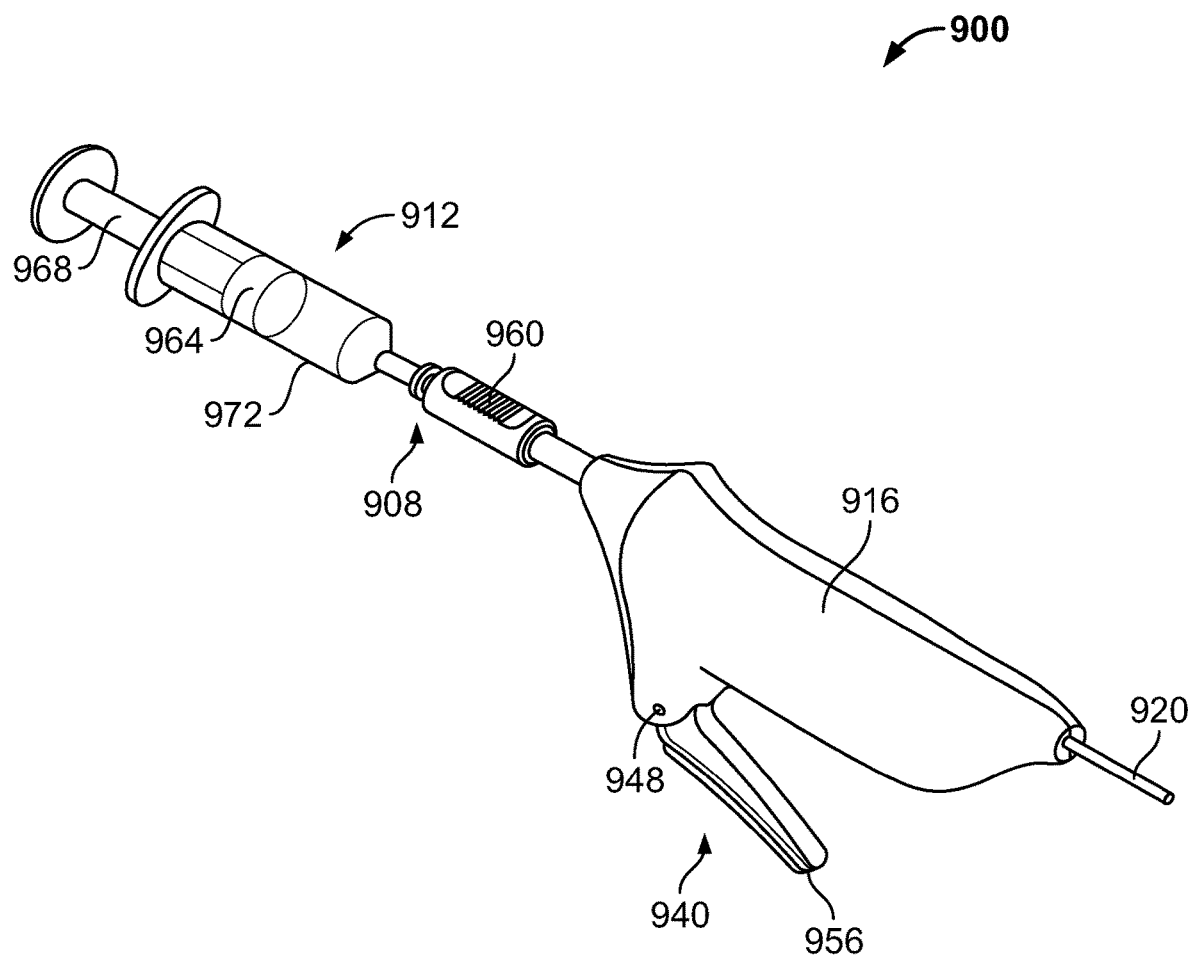
FIG. 15 is a perspective view of one example of a device that implements a suction source and a fluid source into a single housing, in accordance with the teachings of the present disclosure.
Figure 16:
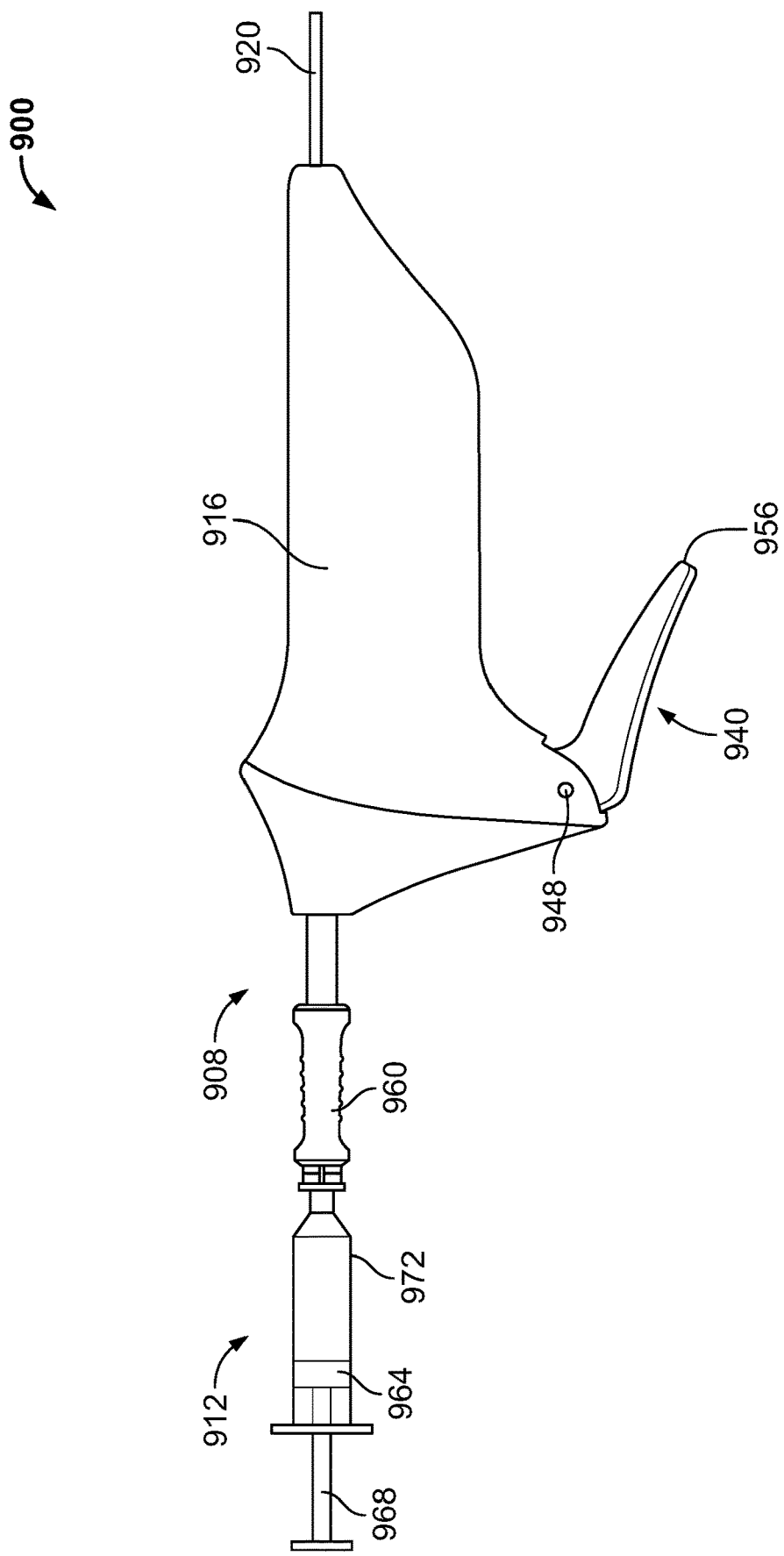
FIG. 16 is a front view of the device of FIG. 15.
Figure 17:
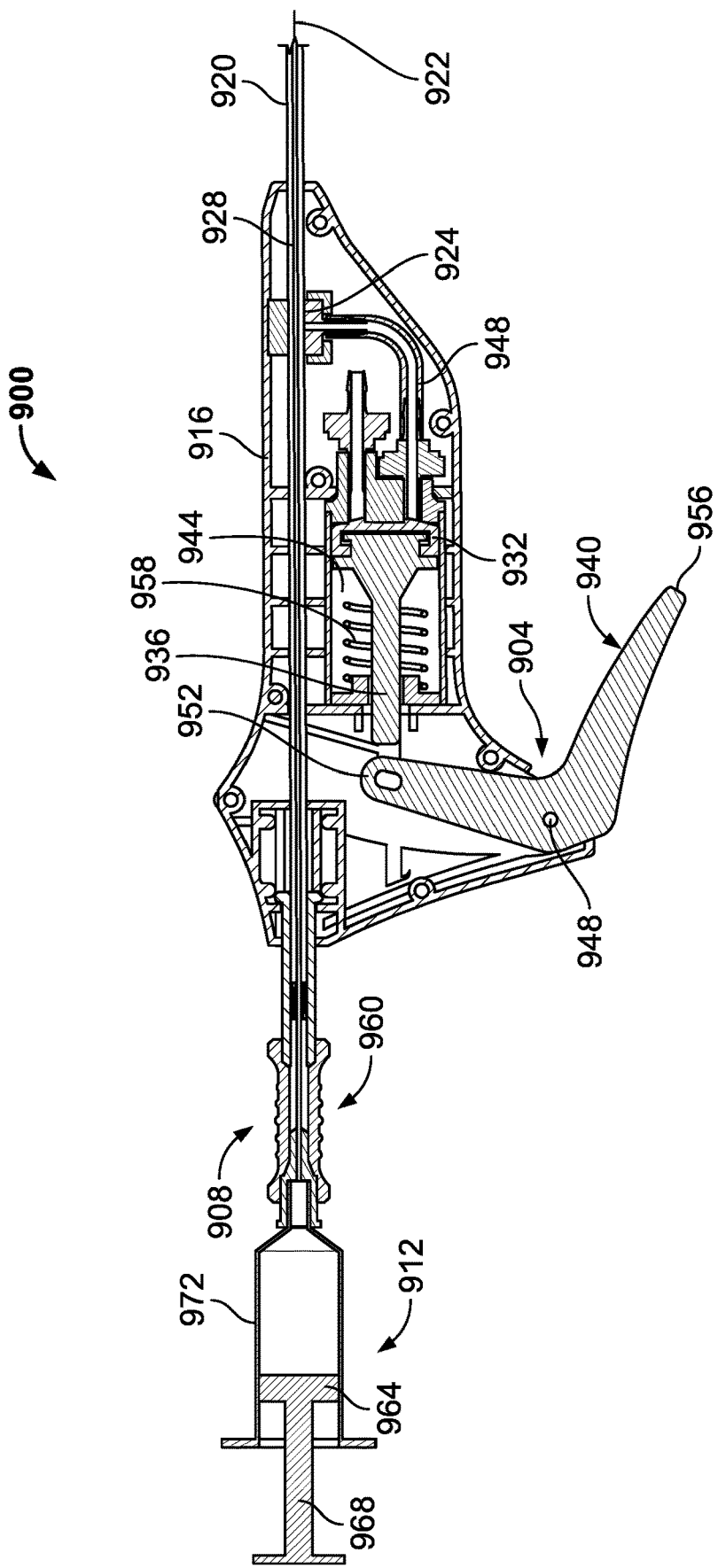
FIG. 17 is a cross-sectional view of the device of FIG. 16.

FIGS. 15-17 illustrate one example of a device 900 that can be used in connection with the endoscopic tool 100 (as well as any of the other endoscopic tools disclosed herein). The device 900 implements a suction source 904 and a fluid injection system 908, which includes a fluid source 912, into a single unit, such that the device 900 can simultaneously serve as the suction source 904 and means for facilitating a quick and easy delivery of the marking fluid 121 into the submucosal layer 108 via the endoscopic tool 100 (or other desired endoscopic tool). In particular, the device 900, via the fluid injection system 908, acts to translate the second cannula 136 forward, to its second position, while the marking fluid 121 is simultaneously injected into the submucosal layer 108.

In this example, the device 900 includes a single, or unitary, housing 916 and a cannula 920 carried by the housing 916 along a longitudinal axis 922 of the device 900. The housing 916 generally has a shape and a size that allow an operator of the device 900 to easily and comfortably grip and operate the device 900. In this example, the housing 916 has the shape and size shown in FIGS. 15-17, though it will be appreciated the shape and/or size can vary. The cannula 920 is generally configured to operatively couple the suction source 904 and the fluid source 912 to the endoscopic tool 100 (or other desired endoscopic tool). While not illustrated herein, it will be appreciated that the cannula 920 can be directly coupled to (e.g., directly inserted into) the endoscopic tool 100 or can be indirectly coupled to the endoscopic tool 100 (e.g., via an adaptor). In either case, the cannula 920 has a first chamber 924 that is arranged to be in fluid communication with the plurality of suction lumens 148 when the cannula 920 is coupled to the endoscopic tool 100, and a second chamber 928 that is surrounded by the first chamber 924 and is arranged to be in fluid communication with the second cannula 136 when the cannula 920 is so coupled. It will be appreciated that the second chamber 928 is fluidly isolated from the first chamber 924 (and vice-versa) in order to fluidly isolate the suction source 904 from the fluid source 912 (and vice-versa).

The suction source 904 in this example takes the form of a hand pump that, when coupled to, for example, the tool 100, is configured to create a negative pressure in the plurality of suction lumens 148 via the first chamber 924. The hand pump includes a valve plug 932, a valve stem 936 coupled to the valve plug 932, and a handle 940 that is coupled to the valve stem 936. The valve plug 932 is movably disposed the housing 916 to control the negative pressure created in the plurality of suction lumens 148. In particular, the valve plug 932 is movably disposed within an annular chamber 944 formed within the housing 916 between a closed position, shown in FIG. 17, in which the valve plug 932 seals a fluid flow passageway 948 that extends between the annular chamber 944 and the first chamber 924 of the cannula 920, and an open position, not shown, in which the valve plug 932 is spaced from the fluid flow passageway 948. The valve stem 936, which may be coupled to the valve plug 932 in any known manner, is movably disposed in the housing 916 as well, with a first portion of the valve stem 936 also movably disposed within the annular chamber 944. The handle 940 is pivotally coupled to the housing 916 about a pivot axis 948 that is perpendicular to the longitudinal axis 922. The handle 940 has a first end 952 that is disposed within the housing 916 and is coupled to an end of the valve stem 936 in any known manner. The handle 940 also has a second end 956 that is disposed outside of the housing 916, such that the handle 940 is partially exposed. The hand pump also includes a biasing element, in this case a spring 958, that serves to bias the valve plug 932 to the closed position.

The fluid injection system 908 is configured to supply the marking fluid 121 to the endoscopic tool 100 via the second chamber 928 of the cannula 920. In this example, the fluid injection system 908 includes a stopper 960, the fluid source 912 containing the marking fluid 121, a plunger 964, and an actuating element 968. The stopper 960 is carried by the cannula 920 at a position outside of the housing 916. The fluid source 912 is coupled to the cannula 920 such that the fluid source 912 is also positioned outside of the housing 916, but further downstream than the stopper 960. In other words, the stopper 960 is disposed between the housing 916 and the fluid source 912. In this example, the fluid source 912 is a syringe 972 that contains the marking fluid 121, though in other examples, the fluid source 912 can take a different form. The plunger 964 is movably disposed within the syringe 972 to help eject the marking fluid 121 from the syringe 972 and into the second chamber 928 of the cannula 920 when desired. Finally, the actuating element 968 in this example takes the form of a handle that is integrally formed with the plunger 964 but extends outside of the syringe 972 to allow the user to actuate the fluid injection system 908 to deliver the marking fluid 121 when desired.

In use, when it is desired to create the negative pressure in the plurality of suction lumens 148, the operator of the device 900 pulls on the exposed portion of the handle 940, which causes the handle 940 to rotate (in a counterclockwise direction when viewed in FIG. 17). This, in turn, causes the valve stem 936 to move, which in turn causes the valve plug 932 to move from its closed position to its open position. In the orientation illustrated in FIG. 17, the valve plug 932 moves leftward within the annular chamber 944 as the valve plug 932 moves from its closed position to its open position. In any case, movement of the valve plug 932 to its open position exposes the fluid flow passageway 948 and draws air from the fluid flow passageway 948 into the annular chamber 944, thereby creating negative pressure in the first chamber 924 of the cannula 920, and, in turn, the negative pressure in the plurality of suction lumens 148.

Meanwhile, to inject the needle 140 into the submucosal layer 108 and inject the marking fluid 121, the user may activate the fluid injection system 908 by, for example, moving the actuation element 968, and, in turn, the plunger 964 forward (i.e., toward the suction surface 144). Moving the actuation element 968 forward moves the plunger 964 forward within the syringe 972, thereby forcing the marking fluid 121 in the syringe 972 through and out of the syringe 972 and into and through the second chamber 928 of the cannula 920, and, in turn, into and through the second cannula 136. Moving the actuation element 968 forward in this manner also simultaneously drives the stopper 960 (and the cannula 920 which carries the stopper 960) forward, toward the suction surface 144, which, in turn, drives the second cannula 136 to its second position, such that the needle 140 is disposed within the enlarged portion 120 and the marking fluid 121 is delivered into the submucosal layer 108 of tissue.

It will also be appreciated that the present disclosure covers other endoscopic tools not explicitly discussed or illustrated herein. For example, in another example of an endoscopic tool not illustrated herein, the endoscopic tool may include a first cannula defined by a pair of tubes co-extruded with one another, with a first of the tubes defining one or more suction lumens, and a second of the tubes defining a fluid lumen separate from the one or more suction lumens. Other examples are envisioned as well.

Turning back to FIGS. 4-7, an example of a method for injecting a marking fluid (e.g., marking fluid 121) into a submucosal layer of tissue (e.g., the submucosal layer 108 of tissue) will now be described. The method utilizes the endoscopic tool 100, though it will be appreciated that the method can utilize any of the tools disclosed herein or a different endoscopic tool to facilitate the injection of the marking fluid into the submucosal layer of tissue.

The method includes disposing a first cannula (e.g., the first cannula 124) within a lumen of an endoscope (e.g., the endoscope 104). The first cannula has a suction surface (e.g., the suction surface 144) disposed at a distal end (e.g., the distal end 146) of the first cannula to contact a mucosal layer of tissue (e.g., the mucosal layer 112 of tissue), a needle stabilization structure (e.g., the needle stabilization structure 168) defining a suction lumen (e.g., the suction lumen 148) formed within the first cannula between the suction surface and a proximal end (e.g., the proximal end 145) of the first cannula, and a fluid lumen (e.g., the fluid lumen 132) separate from the suction lumen. The method includes disposing a second cannula (e.g., the second cannula 136) carrying a needle (e.g., the needle 140) within the fluid lumen of the first cannula.

The method includes moving the first cannula from a first position, whereby the suction surface is disposed within the lumen of the endoscope, to a second position, whereby the suction surface is disposed outside of the lumen of the endoscope and proximate to a target area within a patient (FIG. 4). The method also includes creating a negative pressure in the suction lumen via a suction source (e.g., the suction source 128) coupled to the first cannula, thereby drawing the target area of tissue into contact with the suction surface and holding the target area of tissue against the suction surface (FIG. 5). The method includes moving the first cannula away from the target area, enlarging the submucosal layer of tissue below the mucosal layer of tissue at the target area (FIG. 6). The method includes moving the second cannula from a first position, whereby the needle is disposed inside of the fluid lumen, to a second position, whereby the needle is disposed outside the fluid lumen, causing the needle to pierce the mucosal layer of tissue. The marking fluid is then injected into the submucosal layer of tissue via the needle, thereby raising the mucosal layer of tissue in the target area of tissue (FIG. 7).

Those skilled in the art will recognize that a wide variety of modifications, alterations, and combinations can be made with respect to the above described embodiments without departing from the scope of the disclosure, and that such modifications, alterations, and combinations are to be viewed as being within the ambit of the inventive concept.

The invention claimed is:

1. An endoscopic tool for facilitating injection of a fluid into a submucosal layer of tissue, the tool comprising:
   a first cannula adapted to be slidably disposed within a lumen of an endoscope, the first cannula having a suction surface and a suction lumen, the suction surface disposed at a distal end of the first cannula to contact a mucosal layer of tissue, the suction lumen formed within the first cannula between the suction surface and a proximal end of the first cannula;
   a second cannula adapted to be coupled to a source of a fluid to be delivered to a submucosal layer of tissue below the mucosal layer of tissue, the second cannula carrying a needle at a distal end of the second cannula;
   a needle stabilization structure coupled to the first cannula or the second cannula, the needle stabilization structure defining a fluid lumen and the suction lumen wherein the fluid lumen is separate from the suction lumen, the second cannula slidably disposed within the fluid lumen; and
   a suction source coupled to the first cannula to create a negative pressure within the suction lumen to draw the mucosal layer of tissue into contact with the suction surface and hold the mucosal layer of tissue against the suction surface, wherein responsive to the mucosal layer of tissue contacting the suction surface, the second cannula is movable toward the submucosal layer of tissue, causing the needle to pierce the mucosal layer of tissue and deliver the fluid into the submucosal layer of tissue.

2. The tool of claim 1, further comprising an adhesive applied to the suction surface to hold the mucosal layer of tissue against the suction surface.

3. The tool of claim 1, wherein the needle stabilization structure comprises an annular wall and a rib that extends between an inner surface of the first cannula and the annular wall.

4. The tool of claim 1, wherein the needle stabilization structure comprises an annular wall and a pair of ribs that extends between an inner surface of the first cannula and the annular wall.

5. The tool of claim 1, wherein the first cannula, the needle stabilization structure, and the second cannula are made from an elastic material.

6. The tool of claim 1, wherein the needle stabilization structure is integrally formed with the first cannula.

7. The tool of claim 1, wherein the needle is fixedly attached to the second cannula via a friction fit or a crimp.

8. The tool of claim 1, wherein the needle stabilization structure extends along an entirety of the length of the fluid lumen.

9. The tool of claim 1, wherein the needle stabilization structure partially extends along the length of the fluid lumen.

10. The tool of claim 1, wherein the suction lumen of the first cannula comprises a plurality of suction lumens surrounding the fluid lumen.

11. The tool of claim 1, further comprising a T-connector coupled to the proximal end of the first cannula, the T-connector having a first port coupled to the first cannula, a second port adapted to be coupled to the suction source, and a third port adapted to be coupled to the source of fluid.

12. The tool of claim 1, further comprising: a stopper carried by the second cannula and disposed within the first cannula between the suction source and the proximal end of the first cannula; a spring operatively coupled to the stopper; the source of the fluid; and a plunger movably disposed within the source of the fluid.

13. The tool of claim 12, wherein the stopper sealingly engages an inner surface of the first cannula and an outer surface of the second cannula.

14. The tool of claim 1, wherein the needle stabilization structure and the second cannula are integrally formed.

15. The tool of claim 1, wherein the needle stabilization structure is coupled to the first cannula.

16. The tool of claim 1, wherein the needle stabilization structure is coupled to the second cannula.

17. The tool of claim 1, wherein the suction surface is perpendicular to a length of the first cannula.

18. An endoscopic tool for facilitating injection of a fluid to a submucosal layer of tissue, the tool comprising:
   a first cannula adapted to be disposed within a lumen of an endoscope, the first cannula having a suction surface disposed at a distal end of the first cannula to contact a mucosal layer of tissue, wherein the suction surface is perpendicular to a length of the first cannula;
   a second cannula adapted to be coupled to a source of a fluid to be delivered to a submucosal layer of tissue below the mucosal layer of tissue;
   a needle stabilization structure coupled to the first cannula or the second cannula, the needle stabilization structure defining at least one suction lumen and a fluid lumen separate from each suction lumen of the at least one suction lumen, the fluid lumen disposed centrally within the first cannula, the second cannula slidably disposed within the fluid lumen;

a needle carried by the second cannula, the second cannula movable between a first position, whereby the needle is disposed within the fluid lumen, and a second position, whereby the needle is disposed outside of the fluid lumen; and a suction source coupled to the first cannula to create a negative pressure within the at least one suction lumen to draw the mucosal layer of tissue into contact with the suction surface and hold the mucosal layer of tissue against the suction surface, wherein responsive to the mucosal layer of tissue contacting the suction surface, the second cannula is movable from the first position to the second position, causing the needle to pierce the mucosal layer of tissue and deliver the fluid into the submucosal layer of tissue.

19. The tool of claim 18, wherein the needle stabilization structure defines a plurality of suction lumens.

20. The tool of claim 19, wherein the needle stabilization structure comprises an annular wall and a pair of ribs extending between an inner surface of the first cannula and the annular wall, wherein the annular wall separates the fluid lumen from the plurality of suction lumens, and wherein the pair of ribs separates the plurality of suction lumens from one another.

21. The tool of claim 18, wherein the needle stabilization structure comprises an annular wall and a rib extending between an inner surface of the first cannula and the annular wall.

22. The tool of claim 18, wherein the first cannula, the needle stabilization structure, and the second cannula are made from an elastic material.

23. The tool of claim 18, wherein the needle stabilization structure is integrally formed with the first cannula.

24. The tool of claim 18, wherein the needle is fixedly attached to a distal end of the second cannula by a friction fit or a crimp.

25. The tool of claim 18 further comprising a T-connector coupled to a proximal end of the first cannula, the T-connector having a first port coupled to the first cannula, a second port coupled to the suction source, and a third port coupled to the source of fluid.

26. The tool of claim 18, further comprising: a stopper carried by the second cannula and disposed within the first cannula between the suction source and a proximal end of the first cannula; a spring operatively coupled to the stopper; the source of the fluid; and a plunger movably disposed within the source of the fluid.

27. The tool of claim 26, wherein the stopper sealingly engages an inner surface of the first cannula and an outer surface of the second cannula.

28. The tool of claim 18, wherein the needle stabilization structure and the second cannula are integrally formed.

29. The tool of claim 18, wherein the needle stabilization structure is coupled to the first cannula.

30. The tool of claim 18, wherein the needle stabilization structure is coupled to the second cannula.

31. A method for injecting a fluid into a submucosal layer of tissue using an endoscopic tool, the method comprising: disposing a first cannula within a lumen of an endoscope, the first cannula having a suction surface that is perpendicular to a length of the first cannula and is disposed at a distal end of the first cannula to contact a mucosal layer of tissue, and defining a suction lumen between the suction surface and a proximal end of the first cannula; disposing a second cannula within a fluid lumen separated from the suction lumen by a needle stabilization structure, the second cannula carrying a needle; moving the first cannula from a first position, whereby the suction surface is disposed within the lumen of the endoscope, to a second position, whereby the suction surface is disposed outside of the lumen of the endoscope and proximate a target area within a patient; creating a negative pressure in the suction lumen via a suction source coupled to the first cannula, thereby drawing the mucosal layer of tissue at the target area into contact with the suction surface; moving the first cannula away from the target area, thereby enlarging a submucosal layer of tissue below the mucosal layer of tissue at the target area; moving the second cannula from a first position, whereby the needle is disposed within the fluid lumen, to a second position, whereby the needle is disposed outside of the fluid lumen, such that the needle pierces the mucosal layer of tissue; and injecting the fluid into the submucosal layer of tissue via the needle, thereby raising the mucosal layer of tissue in the target area.

* * * * *